United States Patent [19]

Myers, Jr. et al.

[11] 4,222,800
[45] Sep. 16, 1980

[54] ISOMERIZATION OF ENDO-ENDO HEXACYCLIC OLEFINIC DIMER OF NORBORNADIENE

[75] Inventors: Harry K. Myers, Jr., Aston; Abraham Schneider, Overbrook Hills, both of Pa.

[73] Assignee: Suntech, Inc., Philadelphia, Pa.

[21] Appl. No.: 964,855

[22] Filed: Nov. 30, 1978

[51] Int. Cl.$^2$ .............................................. C06B 23/00
[52] U.S. Cl. .................................. 149/109.6; 60/205; 60/208; 585/14; 585/360
[58] Field of Search .......................... 60/205, 206, 208; 149/109.6; 585/14, 360

[56] References Cited

U.S. PATENT DOCUMENTS 4,086,286   4/1978   Janoski et al. .......................... 60/208

OTHER PUBLICATIONS

Katz, Tetrahedron Letters, No. 27, pp. 2601 to 2605 (1967).
Katz et al., J. Am. Chem. Soc., vol. 91, No. 1, pp. 206 to 208 (1969), Abstracted in Chem. Abs., vol. 70, pp. 265, 87128q.
Acton et al., J. Am. Chem. Soc., vol. 94, No. 15, pp. 5446 to 5456 (1972).

*Primary Examiner*—Leland A. Sebastian
*Attorney, Agent, or Firm*—J. Edward Hess; Donald R. Johnson; Anthony Potts, Jr.

[57] ABSTRACT

The endo-endo olefinic hexacyclic dimer of 2,5-norbornadiene is isomerized using an acidic alumina catalyst. The isomerization temperatures ranges from between about an ambient temperature to about 300° C. The isomerized product, after hydrogenation, can be used as a high density missile fuel.

12 Claims, No Drawings

ISOMERIZATION OF ENDO-ENDO HEXACYCLIC OLEFINIC DIMER OF NORBORNADIENE

BACKGROUND OF THE INVENTION

The invention herein described was made in the course of or under a contract thereunder with the United States Air Force Systems Command.

The invention relates to the isomerization of the olefinic endo-endo homodimer of 2,5-norbornadiene, hereinafter referred to as NN=. Particularly the invention relates to the preparation of an isomeric liquid mixture from NN= using a catalyst.

The aforementioned isomeric liquid mixture, after hydrogenation, can be used as high energy missile fuel in either jet or rocket propulsion. Jet propulsion includes a jet engine which can be used for a missile, an aircraft and others and includes the three basic types, i.e., ramjet, turbojet and pulse jet. The term rocket generally refers to a device containing its own oxygen or oxidizing agent. An article in Aviation Week and Space Technology, Jan. 26, 1976, pages 111-113, discloses some of the high density hydrocarbon fuels that are under consideration as missile fuels.

Norbornadiene (bicyclo-(2.2.1)-2,5-heptadiene) can be prepared by reacting cyclopentadiene and acetylene at an elevated temperature, see U.S. Pat. No. 2,875,256 (Cl. 260-266). Norbornadiene has the following structure:

It can be dimerized into the olefinic endo-endo homodimer (NN=) having the following structure:

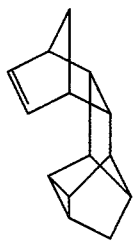

I

Dimerization of 2,5-norbornadiene to compound I is disclosed in "The Stereochemical Course of Metal Catalyzed Cycloaddition Reactions of Norbornadiene", T. J. Katz et al, Tetrahedron Letters, No. 27, pp. 2601-2605, 1967. The dimerization involves the use of a group VIII metal complex.

Among the compounds that can be formed from contacting norbornadiene in the presence of both [C$_6$H$_5$)$_3$P]$_2$RhCl and (C$_6$H$_5$)$_3$P are olefinic norbornadiene homodimer compounds having the following structures II and III.

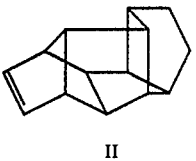
II

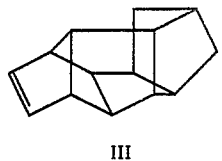
III

This is disclosed in "Dimerization and Trimerization of Norbornadiene by Soluble Rhodium Catalysts," Nancy Acton et al, Journal of the American Chemical Society, 94:15, July 26, 1972. Compound III, along with compound I, is also disclosed in Chemical Abstracts, Vol. 70, 1969, page 265, 87128q. The abstract refers to an article disclosed in Journal of the American Chemical Society, 91:1, Jan. 1, 1969, pages 206-208, "The Reaction of Complexes of Rhodium (I) Chloride with Norbornadiene".

Hydrogenation of compounds I, II, and/or III results in a hydrogenated compound having a high density and a high heat of combustion making them useful as missile fuels. The hydrogenated compound II is referred to hereinafter as HINN, whereas the hydrogenated compound I is referred to hereinafter as HNN.

SUMMARY OF THE INVENTION

NN= is isomerized to various isomers, including a compound having structure II, using a catalytic amount of acidic alumina catalyst. The isomerization temperature is in the range between from about an ambient temperature to about 300° C. The resulting isomer, after hydrogenation, generally has a high density and a high heat of combustion and therefore has use as a missile fuel.

DESCRIPTION

The isomerization of NN= to its isomers, including a compound having structure II, occurs under the hereinafter specified operating conditions and in the presence of an acidic alumina catalyst. The isomers, including compound II, can be hydrogenated in the presence of hydrogen and a conventional hydrogenation catalyst such as a nickel on kieselguhr under mild operation conditions, e.g., a temperature of 120° C. and 100 psig of hydrogen.

The NN= feed can contain other similar hydrocarbons, such hydrocarbons should not adversely affect the isomerization. Further, the similar hydrocarbons should not adversely influence the desired resulting properties of the isomerized mixture. Thus for optimum results, the feed can consist of essentially NN=, however some other isomers of norbornadiene dimer can be present.

The catalyst used to isomerize the NN= is an acidic alumina. The properties and preparation of alumina (aluminum oxide) are well known, for example see Kirk-Othmer, Encyclopedia of Chemical Technology, 2nd Edition, Vol 2, Aluminum compounds. Alumina has many different phases and can be one of the following: alpha or beta trihydrate, alpha or beta monohydrate, alpha, gamma, delta, eta, theta, iota, kappa or chi. Small amounts of other materials, e.g. silica, can be present in the alumina. An acidic alumina is an alumina that has been washed or prepared in an acidic environment. The acid used to form the environment can be sulfuric, hydrochloric, phosphoric and the like. While any of the aforementioned alumina or mixture thereof can be used for the isomerization to isomers including compound II, the preferred aluminas are selected from a group consisting of alpha monohydrate, a mixture of alpha monohydrate and chi, and gamma. The amount of catalyst present in a catalytic amount; thus the amount of alumina present is sufficient to direct the isomerization. However, while a wide range can be used, the preferred catalyst concentration range is between from about one part by weight of catalyst per hundred parts by weight of NN= feed to about a one to one ratio, while a more preferred ratio range is between from about 1:20 to about 1:5.

The isomerization temperature is one at which the isomerization reaction will occur, and generally it can vary between two general limits. A lower limit can be determined by the rate of the reaction, i.e. if the temperature is too low the reaction rate is slow, and such a slow rate makes the process unattractive commercially. Thus, generally the lower temperature limit is about ambient with about 25° C. preferred. The upper temperature limit can be determined by the formation of undesirable materials which adversely affect the properties of the isomeric mixture. Generally the upper temperature limit is about 300° C. with 290° C. preferred.

Pressure can be used during the isomerization. Generally a wide range of pressure can be used, however, economic consideration favors using as low a pressure as possible. A typical pressure range would be between from about atmospheric pressure to about 200 psig.

After the isomerization the catalyst can be separated by various known means from the hydrocarbon product. The hydrocarbon product itself can be separated from any unreacted feed if desired or the isomers can be separated from each other or from other formed compounds. Need for the separation of the product hydrocarbons depends on the specification set for the missile fuel. Hydrogenation of the isomeric product can be performed on the whole product or its separated fractions.

Because of the unsaturation of the isomeric NN=, a tendency exists for the material to form a polymer and/or a gum which can cause mechanical problems. Such a problem in a missile could be very detrimental. Thus, the isomeric NN= is hydrogenated to saturate the double bond, and the hydrogenated isomer, e.g. HINN, is used as a fuel or component thereof.

As disclosed hereinafter the isomers, including the compounds having structures II and III, can be, after hydrogenation, blended with other suitable hydrocarbons. The resulting blends can have use as improved missile fuels. The aforementioned suitable hydrocarbons include saturated pentacyclic homodimers and saturated hexacyclic homodimers of norbornadiene which includes the compound having structure I after hydrogenation. Also exo-tetrahydrodicyclopentadiene (exo-THDCP) is a suitable blending component. Other suitable blending components are known to those skilled in the art.

The following examples are illustrative of the present invention. Also, shown are comparative examples.

EXAMPLES

The accompanying Table I summarizes the operating conditions, conversions and selectivities of runs 1-8. The general procedure used during runs 1-8 was as follows. Acidic alumina and liquid NN= were mixed together in a suitable flask at 24° C. and then deaerated with argon. The acidity of the alumina was believed to be caused by the presence of sulfuric acid. After the deaeration the mixture was heated gradually, over about two hours, to a temperature of about 170° C. or higher. During this period some moisture was driven off. Then intermittent heating occurred over many hours and during that time the temperature was increased to about 200° C. or higher. During the runs the alumina developed an orange color while often the liquid became a lighter yellow. At the end of the run the heating was stopped. After cooling, a sample of the product mixture was analyzed by NMR, mass spectroscopy, infrared analysis, thermogravimetry analysis (TGA) and vpc (vapor phase chromatography). The structure of compound II was found to be as previously shown.

Comparative runs were made. In one run, 61.3 grams of the exo-exo olefinic dimer of 2,5-norbornadiene were heated at 180° C. with 6.1 grams of acidic alpha monohydrated alumina for 22 hours with only a trace of isomerization observed via the vpc. In another run, 1.84 grams of NN= with 0.184 grams 60% nickel on kieselguhr were heated at 177° C. for 16.5 hours with no measurable conversion. Also no measurable conversion was the result when 1.84 grams of NN= were heated at 171° C. without catalyst for 16.5 hours. Finally, no conversions of NN= were detectable via the vpc using various non-acidic aluminas for 11.9 hours at 270° C.

Some of the isomeric mixture from runs 1-8 was completely and rapidly hydrogenated in a rocking bomb using 10 wt.% of powdered 5% rhodium-on-alumina catalyst at a maximum temperature of 125° C. and 100 psig of hydrogen by shaking for about 77 minutes. After filtration of the catalyst the final hydrogenated product was a clear, very pale yellow with an approximate pour point of −25° C. In another hydrogenation run an isomeric mixture was also completely and rapidly hydrogenated using 10 wt.% of nickel-on-kieselguhr at 100 psig of hydrogen and a maximum temperature of 113° C. for two hours. The density of this hydrogenated mixture was 1.1095 and it had a net heat combustion of 163,608 BTU/gallon. Other properties were as follows: viscosity 13.9 cst @ 100° F., and a bromine number of 1.95. In still another hydrogenation run, mass analysis of the hydrogenated HINN indicated that a minor amount of a tetramer ($C_{28}H_{34}$) was present.

Another illustration of the present invention (run 9) involves the formation of a solid isomer. In this run 61.3 grams of NN= were mixed with 12.3 grams of a calcined acidic alumina which was prepared by heating alpha monohydrate acidic alumina for four hours at 700° C. The temperature of the resulting mixture (of NN= and calcined alumina) rose to about 70° C. (without heating), and the alumina formed a dark brown color. After about an hour the temperature of the mixture returned to ambient temperature. Upon heating the cooled mixture to about 50° C. an exotherm occurred and the temperature rose to 250° C. With the unexpected increase in temperature the heating was discontinued. During the subsequent cooling the resulting mixture was too viscous to sample, while after cooling the mixture appeared to be solid.

A portion of the aforementioned solid was found to be soluble in n-pentane or benzene. After percolation of a solution of n-pentane through a commercial acid bentonite clay the resulting solid had a melting point of about 98° to 105° C. The solid was insoluble in water, methanol, and dimethyl ketone. An isomer (not compound II) was also formed but it was not identified.

In still another illustration of the present invention (run 10) NN= was isomerized using a mixture of gamma and chi aluminas which was believed to be acidic because of the presence of hydrogen chloride. The resulting product analysis included compound II and the unidentified isomer of run 9.

The foregoing hydrogenated isomers, II and III after hydrogenation, can be blended with other high density hydrocarbons. For example the hydrogenation and hydrogenolysis of compound I yields the following pentacyclic isomers:

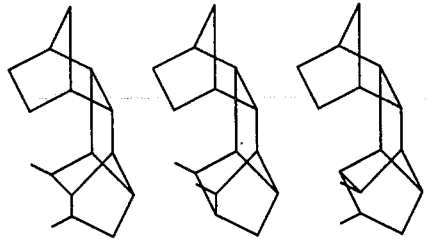

The isomers hereinafter are referred to as PHNN. Hydrogenolysis of saturated compound I is disclosed in applicants' copending application Ser. No. 942,860, filed Oct. 15, 1978.

Various blends of PHNN, HINN, and HNN were prepared to determine use of the blends as a missile fuel. The properties of the blends as well as the particular compounds are reported in the accompanying Table II. The properties include melting point, density, net heat of combustion, and viscosity. As can be seen from Table II, all but two blends have a net heat of combustion in excess of 160,000 BTU/gal which is exceedingly high for hydrocarbons.

Melting points were determined by subjecting the material to prolonged storage at −180° F. and afterwards slowly warming the material until a melting point was determined. However, because the material may have been extremely viscous at the storage temperature, in several instances, (samples 9, 11, 12, 13 & 14) it was not possible to determine if the material froze or remained in a super-cooled stage. Thus, no melting points could be determined.

Use of other acidic aluminas and mixtures thereof will yield analogous isomerization results.

TABLE I

| | | | | | | | | | |
|---|---|---|---|---|---|---|---|---|---|
| | | | | | Isomerization of NN= | | | | |
| Run | NN= Grams | Catalyst Type | Catalyst Amount g | Max. Temp. °C. | Max. Pressure psig | Total Heating Time Hours | % Conversion | % Selectivity II | % Selectivity Other f | % Polymer b |
| 1 | 3270 | a | 131.6 | 207 | 0 | 37.6 | 74.9 | 73.6 | 14.2 | 1.0 |
| 2 | 184 | a | 18.4 | 192 | 0 | 19.5 | 94.2 | 68.0 | 16.6 | — |
| 3 | 18.4 | a | 1.84 | 198 | 0 | 7.4 | 89.0 | 84.3 | 6.7 | 4.2 |
| 4 | 18.4 c | a | 1.84 | 180 | 13 | 7.3 | 90.8 | 68.0 | 19.2* | — |
| 5 | 1124 | d | 200 | 230 | 0 | 15.3 | 84.2 | 54.0 | 37.6 | 1.0 |
| 6 | 36.8 | a | 0.73 | 171 | 0 | 21.4 | 83.8 | 78.2 | 20.1* | — |
| 7 | 2.2 | e | 0.04T | 270 | 0 | 18.6 | 85.6 | 67.1 | 21.6 | — |
| 8 | 2.2 | e | 0.04P | 270 | 0 | 7.8 | 81.6 | 67.3 | 21.0 | — | a Alpha monohydrte acidic alumina.
b Amount of residue after evaporation.
c Includes an additional 6.98g of endo-tetrahydrodicyclopehtane.
d Gamma and chi acidic alumina.
e Acidic gamma alumina and silica.
f = Other Isomer
T = Tablets
P = Powder
*Include two isomers

TABLE II

| | | Properties of Norbornadiene Dimers & Blends | | | | |
|---|---|---|---|---|---|---|
| No. | Hydrocarbon | Melting Point, °C. | Density$^a$ | BTU/GAL$^b$ | Viscosity - Cst@ 77° F. | Viscosity - Cst@ 100° F. |
| 1. | HNN | 11–12 | 1.0839 | 161,278 | 20.77 | 13.49 |
| 2. | PHNN | 4 | 1.0438 | 157,748 | 19.64 | 12.59 |
| 3. | HINN | −18 | 1.1095 | 163,608 | 100.80 | 50.44 |
| 4. | HINN$^c$ | −10 | 1.0875 | 161,461 | 19.76 | 12.84 |

| | BLENDS - (Wt. %) | | | | | | |
|---|---|---|---|---|---|---|---|
| | HNN | PHNN | HINN | | | | |
| 5. | 35 | 65 | — | −12 | 1.0570 | 159,206 | 19.95 | 12.95 |
| 6. | 50 | 50 | — | −34 & −25 | 1.0628 | 160,363 | 20.12 | 13.12 |
| 7. | 65 | 35 | — | −20 | 1.0688 | 160,511 | 20.27 | 13.05 |
| 8. | 75 | — | 25 | −9 | | | | |
| 9. | 35 | — | 65 | * | 1.0998 | 163,269 | 52.28 | 29.49 |
| 10. | 50 | — | 50 | −20 | 1.0964 | 162,791 | 42.10 | 24.43 |
| 11. | 65 | — | 35 | * | 1.0920 | 162,857 | 32.92 | 19.94 |
| 12. | — | 50 | 50 | * | 1.0736 | 160,740 | 37.23 | 21.63 |
| 13. | 33.3 | 33.3 | 33.3 | * | 1.0776 | 161,545 | 31.37 | 19.00 |
| 14. | EXO-THDCP(40 Vol %) | | | | | | | |

TABLE II-continued

| | Properties of Norbornadiene Dimers & Blends | | | | Viscosity - Cst@ | |
| No. | Hydrocarbon | Melting Point, °C. | Density[a] | BTU/GAL[b] | 77° F. | 100° F. |
| --- | --- | --- | --- | --- | --- | --- |
| | & HINN (60 Vol. %) | * | 1.0431 | 155,000(cal) | 15.77 | 10.48 |

[a] d $\frac{20}{4}$ ° C.
[b] net heat of combustion
[c] distilled, without oligomers
*Freezing of the blend during prolonged storage @ −180° F. was not determinable.

The invention claimed is:

1. Process for the isomerization of an olefinic endo-endo hexacyclic dimer of norbornadiene comprising:
   a. contacting a hexacyclic dimer having the following structure:

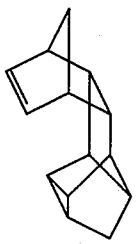

with a catalytic amount of an acidic alumina catalyst; and
   b. having the contacting occur at a temperature in the range from about an ambient temperature to about 300° C.; and
   c. continuing the contacting until an isomer of the olefinic endo-endo hexacyclic dimer of norbornadiene is formed.

2. Process according to claim 1 wherein the acidic alumina catalyst is selected from the group consisting of alpha-monohydrate alumina, a mixture of alpha-monohydrate alumina and chi alumina, and gamma alumina.

3. Process according to claim 2 wherein a formed isomer product has the following structure:

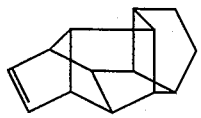

4. Process according to claim 1 wherein the acidic alumina catalyst is a calcined acidic alpha monohydrate alumina.

5. Process according to claim 4 wherein an isomer product is formed which is a solid at ambient temperature.

6. Process according to claim 5 wherein the solid is an oligomer and is soluble in n-pentane or benzene.

7. Process according to claim 1 wherein the temperature range is between from about 25° C. to about 290° C.

8. Process according to claim 7 wherein the amount of catalyst present is in the range between from about 1 part to about 100 parts by weight of dimer to about one part to about one part by weight of the dimer.

9. An improved missile fuel comprising a saturated isomerized norbornadiene dimer having the following structure:

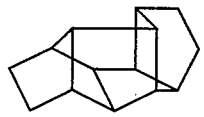

10. Fuel according to claim 9 wherein in addition is present a saturated norbornadiene dimer having the following structure:

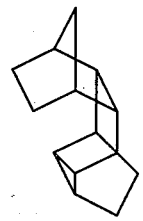

11. Fuel according to claim 10 wherein in addition is present at least one of the following pentacyclics:

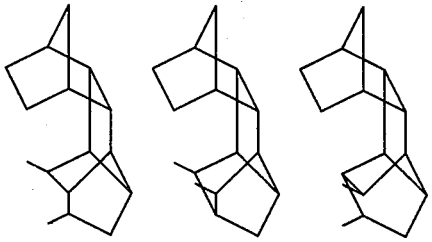

12. Fuel according to claim 11 wherein in addition is present exo-tetrahydrodicyclopentadiene.

* * * * *